United States Patent [19]

Blomberg et al.

[11] Patent Number: 5,781,024
[45] Date of Patent: Jul. 14, 1998

[54] INSTRUMENT PERFORMANCE VERIFICATION SYSTEM

[75] Inventors: Scott E. Blomberg, Madison, Wis.; James D. Kurkowski; David J. DeRoode, both of Minnetonka, Minn.

[73] Assignee: Diametrics Medical, Inc., Roseville, Minn.

[21] Appl. No.: 687,687

[22] Filed: Jul. 26, 1996

[51] Int. Cl.⁶ ............................ G01R 31/02; G01R 35/00
[52] U.S. Cl. .................... 324/763; 324/601; 324/537; 204/406
[58] Field of Search ........................ 324/439, 537, 324/601, 763, 71.1; 436/149; 204/403, 406

[56] References Cited

U.S. PATENT DOCUMENTS

| | | | |
|---|---|---|---|
| 3,874,850 | 4/1975 | Sorensen et al. | 324/439 X |
| 4,557,269 | 12/1985 | Reynolds et al. | 128/675 |
| 5,096,669 | 3/1992 | Lauks et al. | 324/439 X |
| 5,124,661 | 6/1992 | Zelin et al. | 324/601 |
| 5,282,950 | 2/1994 | Dietze et al. | 204/406 |
| 5,320,732 | 6/1994 | Nankai et al. | 204/403 |
| 5,366,609 | 11/1994 | White et al. | 204/403 |
| 5,695,623 | 12/1997 | Michel et al. | 204/403 |

*Primary Examiner*—Glenn W. Brown
*Attorney, Agent, or Firm*—Haugen and Nikolai, P.A.

[57] ABSTRACT

A device and method for testing and monitoring, either manually or automatically, the performance of various components electrically linked to the electronic circuitry of a diagnostic instrument. Components of the electrical circuitry, including potentiometric operational amplifiers and a multi-channel connector, are tested for leakage current, A/D reference voltage, edge connector contact resistance and background noise.

28 Claims, 8 Drawing Sheets

INSTRUMENT PERFORMANCE VERIFICATION SYSTEM

BACKGROUND OF THE INVENTION

I. Field of the Invention

This invention relates generally to diagnostic testing instruments, and more particularly, to an electronic system and method incorporated integral to the diagnostic instrument for verifying the performance of the instrument. The instrument performance verification system is activated periodically or manually to detect any changes in the integrity of the diagnostic instrument, thereby assuring and maintaining the accuracy of the analysis conducted by the diagnostic instrument.

II. Discussion of the Related Art

In order to confirm that a diagnostic instrument is operating to specification, controlled tests must be run periodically on the diagnostic instrument. In the past, standardized control samples of known composition have been used to determine whether the diagnostic instrument is operating as expected. A blood analyzer is one example of a diagnostic instrument that may use standardized control samples to determine its operating quality. The typical blood analyzer has electrochemical sensors that are used to test for blood constituents such as blood gases and other species in a sample.

Diagnostic systems are known in which a plurality of electrochemical sensors have been built into a single use disposable cartridge. These sensors can be used to make a variety of measurements when in contact with, for example, a sample of blood. The hematocrit, for example, of the blood may be measured by determining the impedance (or its inverse, conductance) of the blood as measured between two electrodes of an electrochemical sensor.

A test unit for a system of this type is disclosed by Zelin et al. in U.S. Pat. No. 5,124,661. In that device, a re-usable plug-in test cartridge is used that introduces externally generated signals of known values that mimic several expected sensor signals to the diagnostic instrument. If the analyzing sensors and circuitry of the instrument are functioning properly, the expected signal output for each will be displayed.

The system disclosed by Zelin et al. impresses simulated signals produced either from a single source and voltage divider resistor network using matched resistors or a second resistor network using multiple tied voltages. These networks supply a voltage step or multiple voltages to an amplifier or open circuit for testing. Simple resistors are employed to produce high impedance. Low voltage signals for simulating signals are produced by amperometric, conductometric and potentiometric sensors. Thus, although the test cartridge system of Zelin et al. permits detection and discrimination between failures from damaged CMOS amplifiers and failures from current leakage in contaminated connectors, that system does not test for circuit leakage, leakage current, A/D reference voltage, temperature control, and edge connector contact resistance.

A pressure transducer incorporating an internal control circuit has been disclosed by Reynolds et al. in U.S. Pat. No. 4,557,269. In Reynolds et al.'s system, the entire pressure transducer is discarded after one use, requiring calibration of the instrument before each test. The required calibration is patient specific and is not interchangeable between patients. Additionally, although the transducer includes an electronic circuit having calibration resistors, the electronic circuit does not verify instrument performance. By testing for leakage to ground, pin to pin and background leakage, all potential areas of failure due to leakage would be identified. Hence, a system that tests for all types of leakage current would be beneficial.

Advantageously, a performance verification system for such a diagnostic instrument would include an integral system that automatically determines the integrity of all aspects of the associated instrument, particularly a user friendly system that minimizes the need for externally connected testing devices. It would also be an advantage if each test signal were independently generated and not based on a common signal input. Further, it would be desirable for the test range to exceed the voltage/amperage range produced by the electrochemical sensors.

SUMMARY OF THE INVENTION

The present invention overcomes the above and other disadvantages of present diagnostic instrument verification systems by providing a more comprehensive, user friendly system and method of verifying the performance and integrity of a portable diagnostic instrument of the class including those for rapid blood analysis using single use plug-in cartridges. Generally, a diagnostic instrument incorporating the system of the present invention includes a housing, a multi-channel connector, an electronic circuit board, a power supply, a control panel, an instrument performance verification system for analyzing output signals, and user interface or output means to indicate results obtained from said instrument performance verification means. An external test cartridge is required to test the temperature control and edge connector contact circuit. The other verifications performed by the system are performed without the necessity of external components.

The diagnostic instrument of the preferred embodiment uses electrochemical methods of sample testing. Certain species within the sample are identified by potentiometric sensors and other species are identified by amperometric sensors.

With amperometric sensors, a potential is generated across a working electrode and a reference electrode. The reference electrode is set to a first potential and stabilized by a counter electrode used to source the current. The potential between the electrodes causes a chemical reaction to occur proximate the electrode surfaces. The electrodes and generated potential are selected such that the current generated across the electrodes is proportional to the amount of the selected analyte present in the sample.

To ensure that the amperometric sensor circuit is functioning properly, a DAC voltage is applied through a resistor of known resistance and the output is applied to the amperometric sensor input (at the working electrode). The sensor circuit output is measured and compared to an expected value and a range of inputs are tested to assure linearity over the entire circuit's range.

To ensure that the potentiometric sensors are functioning properly, the potentiometric operational amplifiers are tested at levels that exceed expected operating levels, thereby verifying that the operational amplifiers exceed the requirements necessary to measure the outputs from the potentiometric sensors. A DAC voltage is directed through a resistor of known resistance and the output is applied to the selected operational amplifier. The output from the operational amplifier is measured and compared to the expected value.

The multi-channel connector is fixed to the housing as part of a system designed for mechanical and electrical connection to a multi-function disposable sensor cartridge device. The electronic circuit board within the diagnostic instrument is electrically coupled to the multi-channel connector and power supply, and is contained within the housing. The electronic circuit board includes a means for analyzing output signals transmitted through said multi-channel connector and other components of the electronic circuit.

The instrument performance verification system of the present invention is a software controlled system that utilizes digital-to-analog converters (DACs) to apply voltages to measure high impedance regions and detect leakage current between channels. The DAC signal is generally a higher voltage signal than those produced by electrochemical sensors. DACs are further used to provide a low impedance signal for performance checking or checking the operation of the front-end amplifier system. Each signal is generated separately and is not tied to any other. The software determines the value of each applied signal. While the test signal sources connect to common conductors, the test signals are not sent through a mechanical connector device.

The verification system may include but is not limited to one or more of the following subsystems: a means for testing a calibration of the cartridge temperature control system, means for detecting leakage to ground within the electronic circuit, means for detecting failure in operational amplifiers electrically coupled to the electronic circuit, means for detecting leakage between pins electrically coupled to the electronic circuit, means for determining failure in an amperometric sensor circuit, means for determining failure in an operational amplifier electrically coupled to the electronic circuit, means for determining failure in a conductivity sensor circuit, means for detecting failure in an AC source of a conductivity sensor circuit, and means for detecting failure in a band pass filter of a conductivity sensor circuit.

The electronic circuitry of the verification system is electrically coupled to a display or output means that indicates performance verification results. In operation, normally, the user activates the test sequence from a control panel, thereby initiating the internal test sequence to test the circuit integrity and performance of the diagnostic instrument.

The internal test routine includes the following steps: activating a test cycle, measuring various amounts of leakage current within the electronic circuit, analyzing the various amounts of measured leakage current, and indicating the results obtained from analyzing the various amounts of leakage current. Other tests may include determining the A/D reference voltage of the electronic circuit, comparing the A/D reference voltage with a predetermined expected value, determining an integrity of the potentiometric sensor circuit (referred to as an Ion Selective Electrode (ISE) in the drawings) operational amplifier electrically coupled to the electronic circuit or other potentiometric circuit operational amplifier, comparing the integrity of the potentiometric circuit operational amplifier with a predetermined expected value, testing the performance of an amperometric sensor circuit, testing the performance of a hematocrit sensor circuit, testing a temperature control circuit coupled to the electronic circuit, and measuring an edge connector contact resistance of said electronic circuit. The internal tests allow the diagnostic instrument to be checked periodically or manually to insure that the circuitry and connectors are functioning properly, thereby avoiding inaccurate diagnostic measurements.

OBJECTS

It is accordingly a principal object of the present invention to provide a performance verification system for a diagnostic instrument that automatically checks the performance of the electronic circuitry and electrical connections of the instrument.

Another object of the present invention is to provide a method of internally checking the integrity of the electronic circuit.

Still another object of the present invention is to provide a passive external card for verifying the performance of the temperature control and edge connector contacts.

Yet another object of the present invention is to provide a diagnostic instrument that includes an internal means of checking the performance of the electronic circuit.

These and other objects, as well as these and other features and advantages of the present invention will become readily apparent to those skilled in the art from a review of the following detailed description in conjunction with the accompanying claims and drawings in which like numerals in the several views refer to corresponding parts.

DETAILED DESCRIPTION

Figure 1:
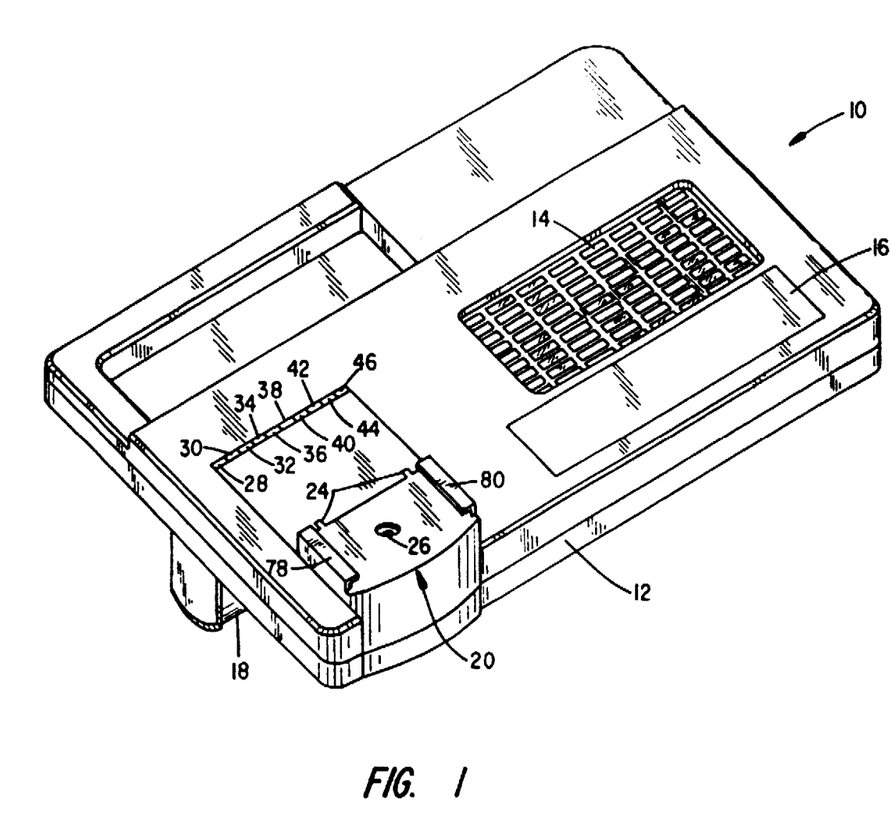
FIG. 1 is a perspective view of an analytical instrument which may incorporate the instrument performance verification system of the present invention.
Figure 6:
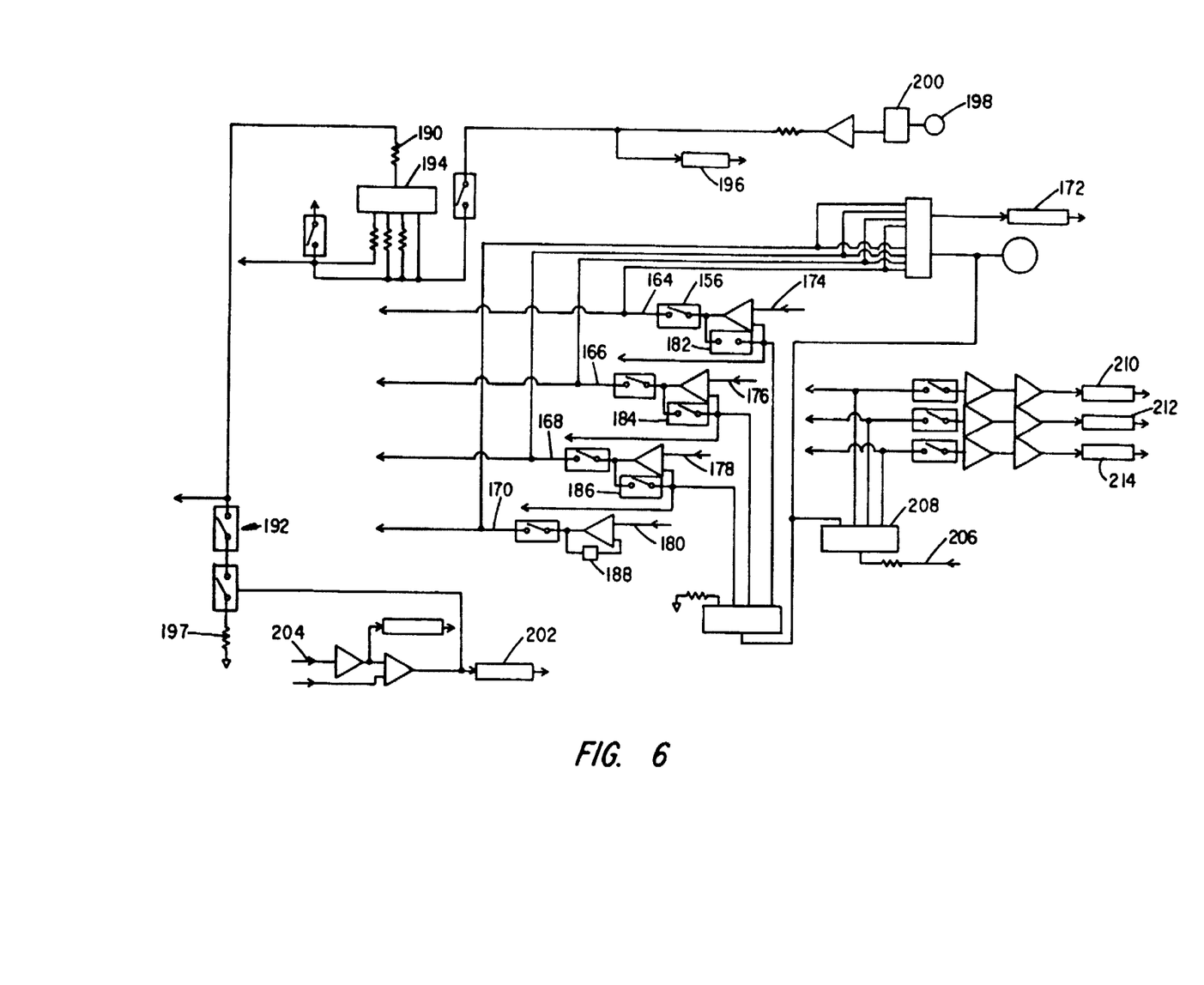
FIGS. 6–7 together present a schematic diagram of a portion of the electronic circuit of the performance verification system of the present invention.
Figure 7:
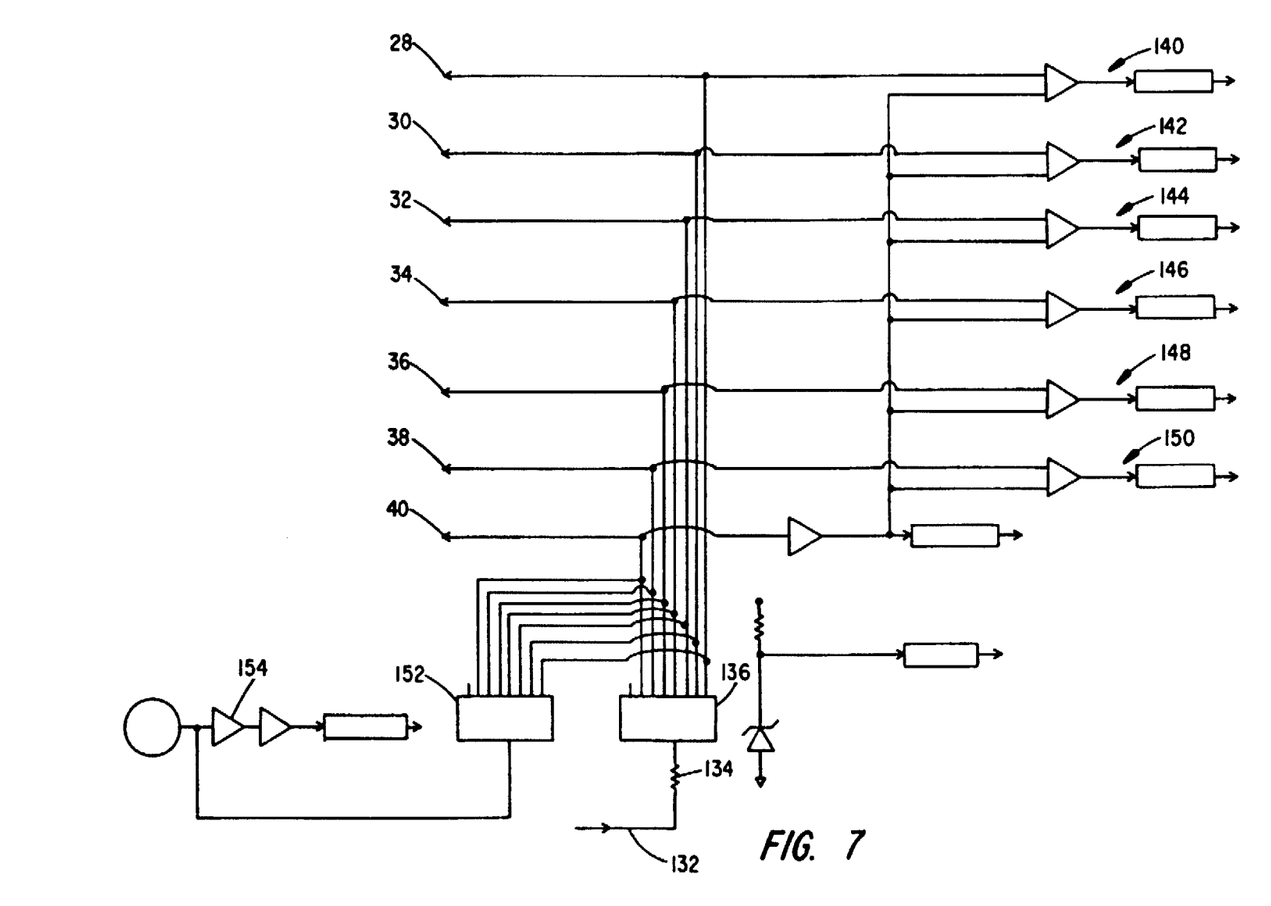

In conjunction with the several views of the figures, details of representative embodiments will next be presented. FIG. 1 shows generally a diagnostic instrument 10 which incorporates the electronic instrument performance verification system of the present invention. The diagnostic instrument 10 includes a housing 12, display 14, control panel 16, power supply 18, cartridge receptacle 20, cartridge temperature control contacts 24, infrared (IR) probe 26, an array of card or cartridge connector contacts 28–46, and electronic circuit (not shown). FIGS. 6–7 illustrate details of the portion of the electronic circuitry used to verify instrument performance.

Figure 2:
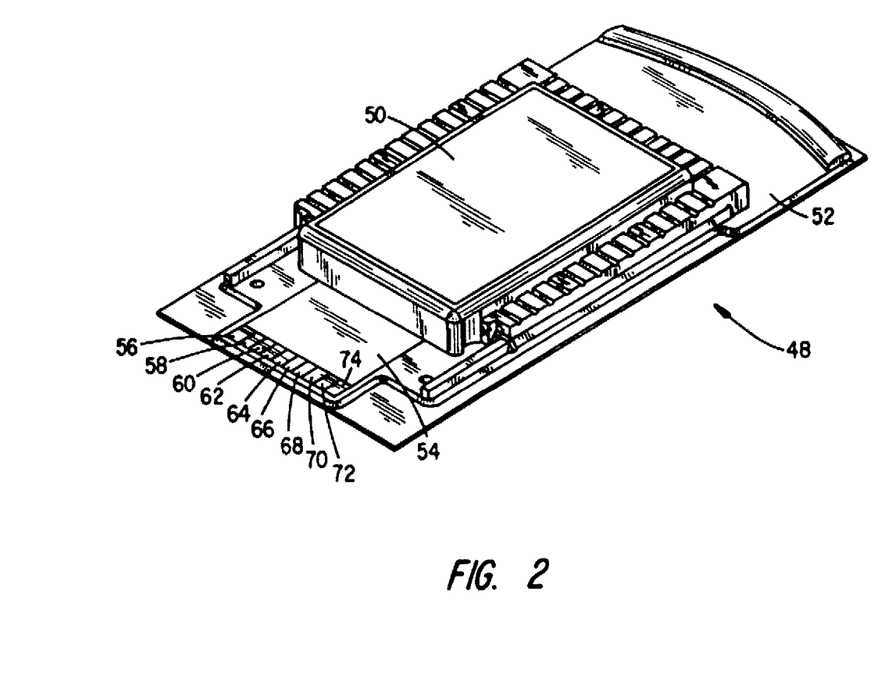
FIG. 2 is a perspective view of a test card used to verify the calibration of the temperature control system and performance of edge connector contacts of the instrument.
Figure 3:
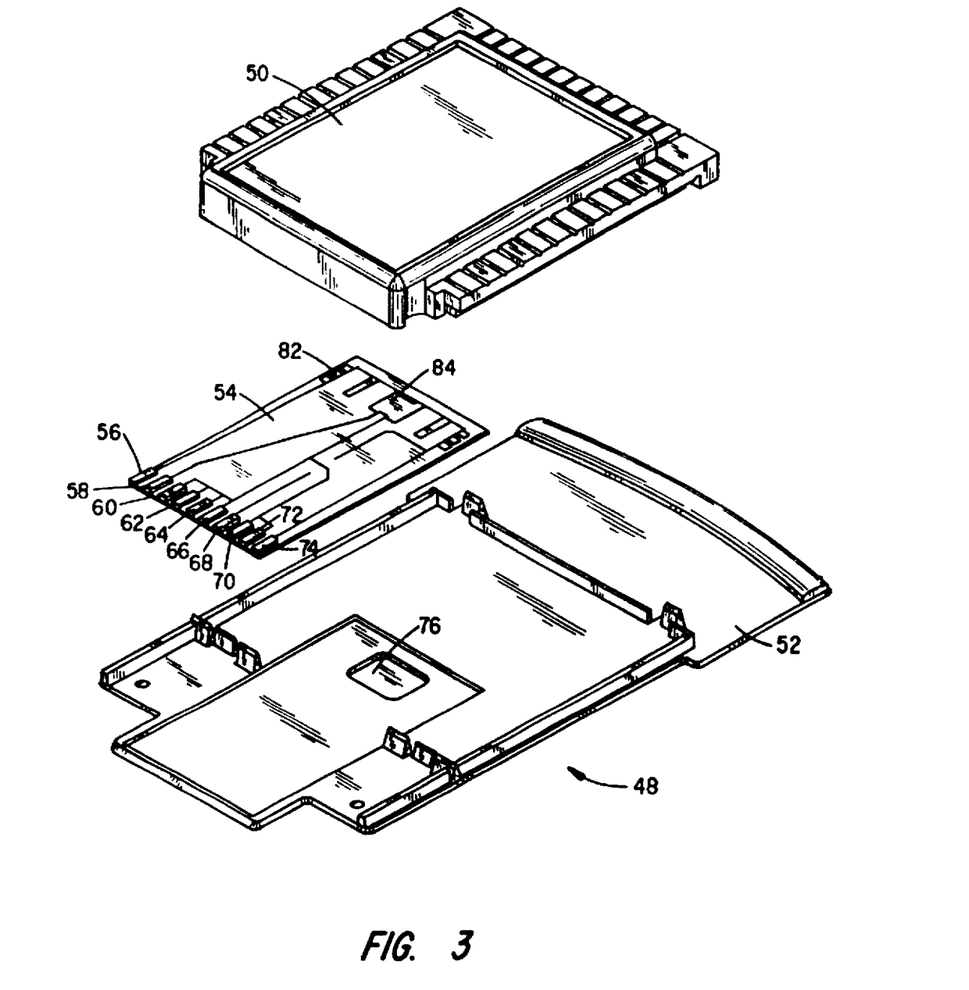
FIG. 3 is an exploded view of a test card of the type shown in FIG. 2.

FIG. 2 and 3 together show the test card used to verify the performance of the temperature control system and edge connector contacts of the diagnostic instrument 10. The test card 48 includes a cover 50 and base 52. A test circuit board 54 is retained between the cover 50 and base 52. An end of the circuit board 54 having lead connector pads 58–74 extends and protrudes beneath the cover 50. An IR transparent probe window 76 (see FIG. 3) is provided in base 52 to enable temperature sensing of the test circuit board 54. Guide rails 78 and 80 guide the test card 48 into contact with the diagnostic instrument 10, wherein the connector contacts 28–46 engage the lead connector pads 56–74. When the test card 48 is engaged with or plugged into the diagnostic instrument 10, the IR probe window 76 aligns with the IR probe 26, allowing IR probe 26 to sense the temperature of the test card circuit board 54. Resistive heaters 82 electrically coupled to the ceramic test circuit board, are used to heat the board 54 to a control temperature. The temperature of the board 54 is also measured by a thermistor 84, and the thermistor signal is compared to the corresponding value sensed by the IR probe as a check on the performance of the IR probe 26.

Figure 4:
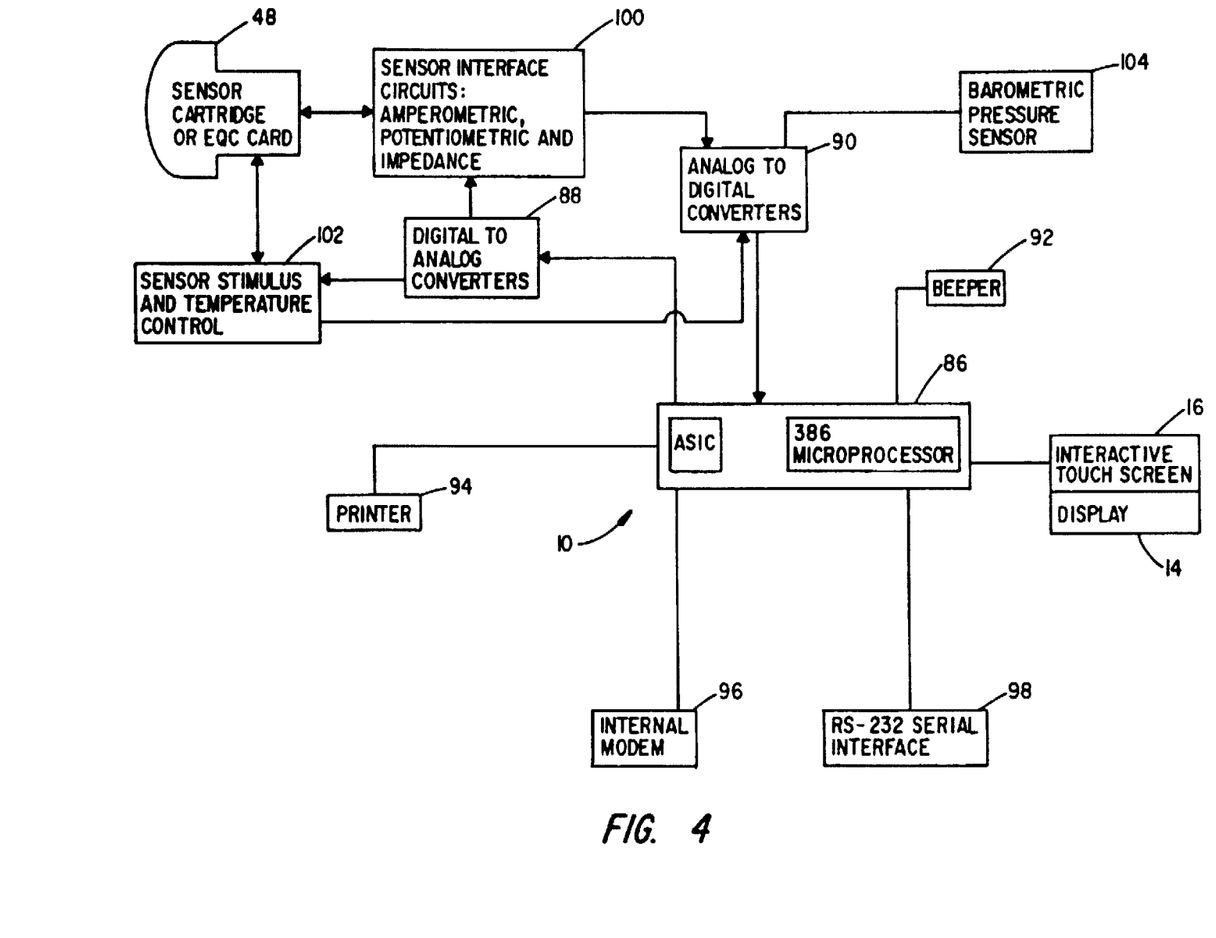
FIG. 4 is a schematic block diagram showing elements of a system employed in carrying out the invention.

FIG. 4 further identifies the various components of the electronic circuit of the diagnostic instrument 10 of the present invention. As discussed below in greater detail, an integrated circuit 86 is electrically coupled to the display 14, control panel 16, digital to analog converters (DACs) generally represented by numeral 88, analog to digital (A/D) converters generally represented by numeral 90, beeper or alarm 92, printer 94, internal modem 96, and serial port interface 98. The DACs 88 are electrically coupled to the sensor interface circuits 100 and temperature controls 102. A barometric pressure sensor 104 is coupled to the A/D converter 90.

Figure 5:
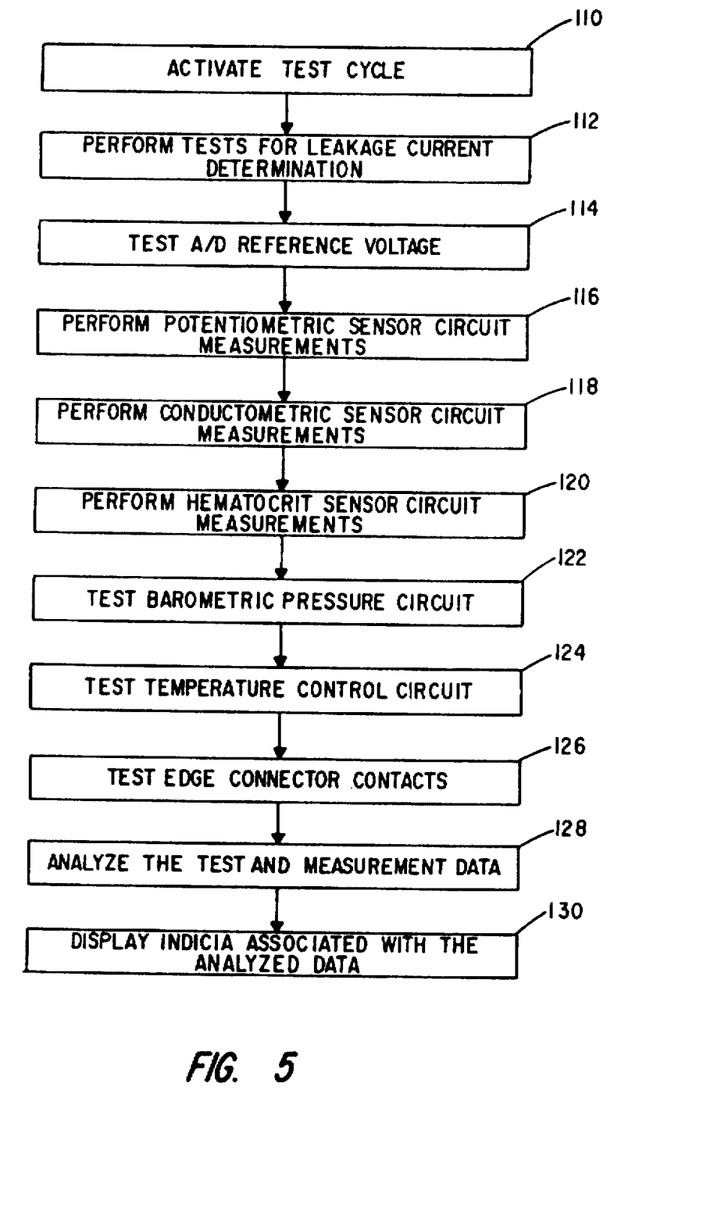
FIG. 5 is a flow chart showing a test routine for the performance verification system of the present invention.

An overview of the process steps for controlling the verification system of the present invention is represented in block form by the flowchart of FIG. 5. The user activates the test cycle using the control panel 16 (see block 110). When the test cycle has been activated, a message will appear on the display 14, prompting the user to remove all sensor cartridges inserted in the diagnostic instrument 10. The instrument performance verification system checks to make sure that the connector contacts 28–46 within the cartridge or card receptacle 20 are open. Alternatively, the test cycle may be activated automatically when a cartridge is removed from the cartridge receptacle 20, when a test card is inserted and the instrument is energized, or when the diagnostic instrument 10 is otherwise energized.

The entire test routine is preferably implemented automatically once a cartridge is removed from the cartridge receptacle 20. A prompt on the display 14 may change, indicating to the user the progress of the test. At the end of the test, the results are indicated on the display 14 and optionally printed on an attached printer 94. Preferably, the results are also stored within internal memory of the integrated circuit 86 for later recall or for down-loading to an external data management system or information system, thereby allowing the user to document and maintain test records. If the test indicates a failure of components of the diagnostic instrument 10, instructions may appear on the display 14, instructing the user on how to proceed to repair the failed components or device. Error codes giving specific failure information are stored for later recall, to assist in further diagnosing any problems detected.

Generally, as depicted in the chart of FIG. 5, once the test cycle has been activated, the system is first directed to test for leakage current within the internal electronic circuitry of the instrument 10 and the connections to the instrument 10 (see block 112). Leakage current within the circuitry may include background leakage, sensing-circuit leakage, pin to pin leakage, and/or pin to ground leakage. The A/D reference voltage is also determined and compared with the expected value at block 114. Accuracy of the A/D reference voltage is important since the measurements made by the instrument are based on the A/D reference voltage.

As further described below, the integrity of each potentiometric circuit operational amplifier is tested at block 116.

They are tested at levels that exceed expected operating levels to verify that the potentiometric circuit operational amplifiers exceed the requirements necessary to measure potentiometric sensor outputs. Various tests to determine the condition of the amperometric and conductometric (possibly hematocrit) sensor circuits are also performed to ensure that those sensor circuits are within predetermined tolerances at blocks 118 and 120. The barometric pressure circuit of barometer 104 is tested at 122.

A prompt next appears on the display 14, instructing the user to insert a test cartridge or card 48. Once the test card 48 is inserted into the cartridge receptacle 20, the temperature control circuit is tested to make sure that the temperature calibration is consistent with the actual temperature of the card 48 determined by the thermistor 84 on the test card 48 (see block 124). The edge connector contacts are also tested to determine the integrity of the contacts at block 126. Once the tests and measurements or comparisons have been performed and processed at 128, a message corresponding to any necessary action required of the user is indicated on the display 14 at block 130.

FIGS. 6–7 together represent a schematic of a portion the electronic circuit that those skilled in the art will recognize as useful to perform the various tests described above. Immediately below is a more detailed discussion of the various diagnostic tests, with reference to the portion of the electronic circuit used to conduct the related test.

A portion of the circuit shown in FIG. 7 is used to detect leakage current from sensor connector contacts 28–46 to ground. At times the area between each sensor contact 28–46 and ground path may become contaminated, creating a leakage path between the contacts and ground path. Leakage between the contacts 28–46 and ground causes an incorrect measurement of the potential, thereby distorting related measurement values. In order to detect leakage between the contacts 28–46 and the ground path, a digital to analog convertor output from DAC 132 of 0.010 Volts (10 mV) is directed through a 1.0M ohm resistor 134 and multiplexor 136 to the potentiometric sensor connector, for example contact 28. The current at the sensor connector is measured and compared to the expected value of 10 n Amps. If the measured current is lower than expected, a leakage path is likely between the sensor connector and the ground path. The accuracy of this detection method is not affected even when the potential directed through the sensors approximates the ground potential.

A portion of the circuit used to detect leakage between contacts is also shown in FIG. 7. Contamination and, hence, leakage between the contacts 28–46 may cause an incorrect measure of potential, current or both, thereby leading to inaccurate output. Contamination between the various sensor's connectors or contacts 28–46 may be detected by directing an output signal from DAC 132 of, for example, 1.0 volts through 1.0 M ohm resistor 134 and multiplexor 136 to a first selected contact, for example contact 30. The current at a corresponding potentiometric sensor lead 142 is measured and compared to the expected value of less than 0.1 n Amps. If a leakage is present between the two selected sensor contacts, the measured current value will be greater than expected. If a leakage between sensor contacts is present, the specific sensor contact is identifiable. By pinpointing specific sensor to sensor contact leakage paths, one can be especially sensitive to those leakage paths that are known to give difficulties in performance.

The portion of the electronic circuit used to detect failure in the potentiometric sensor operational amplifiers within the electronic circuit is further shown in FIG. 7. Electrostatic discharge (ESD), for example, within the integrated circuit may damage the operational amplifiers. In order to detect damage to the operational amplifiers, a DAC voltage from DAC 132 is directed through 1M ohm resistor 134 and through multiplexor 136 to operational amplifiers 140–150. The output is measured and compared to the expected value.

The potentiometric reference electrode contact 40 must be at ground potential, since all contact measurements are performed with respect to the reference electrode. The provided DAC voltages should span a range that exceeds the expected range of the sensor outputs to sufficiently test the limits of the circuits. Several measurement points should be used over the range to confirm linearity of the relation over the entire circuit range. By testing the circuit in a manner that exceeds the requirements necessary to measure potentiometric sensor outputs, the chances of identifying or catching a sensor circuit that is marginal is improved.

FIG. 6 shows a portion of the electronic circuit used to determine failure of any switches or operational amplifiers corresponding to DAC bias output switches 156–162 used to set the amperometric sensor bias and source current within the electronic circuit. To detect such a failure, an MF pin 164–170 associated with each switch is connected to an A/D converter 172 which is monitored. The DAC bias 174–180 is set to a predetermined value, preferably 2 Volts. When each of output switches 156–162 is closed and the circuit is operating properly, the control monitor reading corresponding to each switch equals the DAC bias output ±tolerance. When each output switch 156–162 is open, the value indicated on the control monitor or display should be zero. Then when each corresponding feedback switch 182–188 is open the monitor reading should be ±rail (2.5 Volts).

FIG. 6 also illustrates a portion of the electronic circuit used to determine failure in a conductometric resistance measurement within the electronic circuit. A resistor divider method is used to determine the conductance. In order to detect damage to the resistor 190, the output from the heater low control 192 is connected to multiplexor 194. The output from the multiplexor 194 is monitored through A/D converter 196. In use, the heater low control 192 is connected to ground through resistor 197, and then the output from the 1K resistor 190 is monitored and compared to expected results.

The top portion of the circuit in FIG. 6 is a portion of the electronic circuitry used to detect failure in the AC source 198 or band pass filter 200 of the hematocrit sensor within the electronic circuitry. Electrostatic discharge, for example, may damage the clock, causing the AC source 198 to clock incorrectly or the band pass filter 200 may center on the wrong frequency. In order to detect damage to the clocks, the output of the bandpass filter 200 is connected directly to the DC converter producing a signal represented as RMS/DC. The RMS/DC signal is sent to a serial A/D 196 which is connected to the display 14.

In use, the Band Pass Filter 200 is set to a desired frequency, for example 71 kHz, and then the AC source 198 is adjusted over several frequencies including those above, below and at the desired frequency. The RMS/DC signal is then monitored for desired results. If the AC source 198 is functioning properly, the 71 kHz RMS/DC signal will correspond with the "71 kHz" AC source signal. The AC source 198 is then set at the desired frequency, for example 71 kHz, and the Band Pass Filter 200 is adjusted over several frequencies including those above, below, and at the desired frequency. The RMS/DC signal is then monitored for desired results. If the Band Pass Filter 200 is functioning properly, the 71 kHz RMS/DC signal will correspond with the "71 kHz" Band Pass Filter signal.

Figure 8:
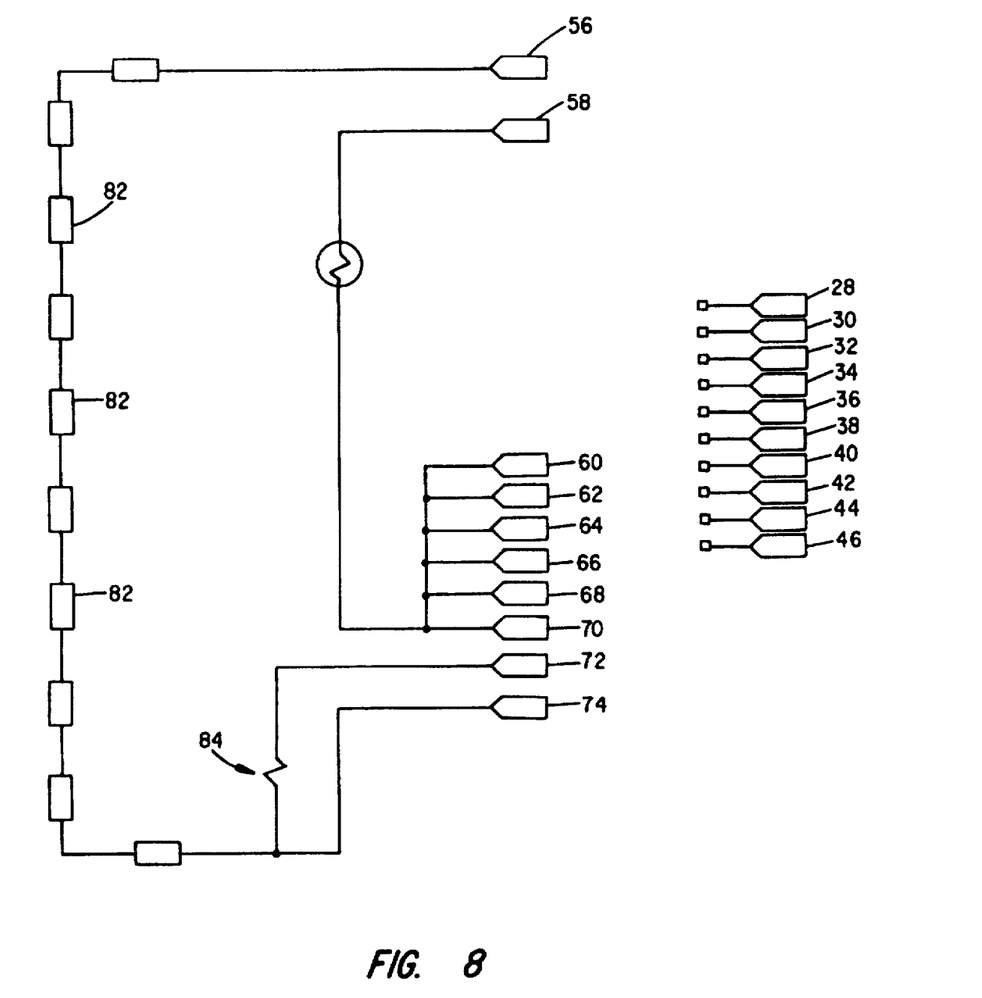
FIG. 8 is a schematic diagram of the electronic circuit of the test card of FIGS. 2 and 3.

The circuit used to detect failure in the temperature control system is illustrated in FIGS. 6 and 8. Temperature control failure may be caused, for example, by a damaged operational amplifier or obstruction of the infrared probe 26. To test the temperature control system, a test card 48 is inserted into the cartridge receptacle 20. The test card 48 circuitry shown in FIG. 8 includes heaters 82 connected in series to simulate a resistance heater contained in an actual diagnostic cartridge. A thermistor 84 is also connected to the test card circuitry, wherein a signal corresponding to the temperature of the card is transmitted to A/D converter 202. The temperature controller is activated to heat to a desired set point, normally 37° C. for processing bodily fluid samples. Once the set point has been reached, the temperature value of the thermistor signal is determined and compared with that of the IR probe output 204. If the value indicated by the thermistor and that of the IR probe output 204 deviate beyond a predetermined margin of error, a temperature control failure message will be displayed on the monitor. The tolerance typically used is ±0.5° C.

An output from the amperometric sensor circuit is measured to determine whether a failure condition exists in that portion of the circuit. In this manner, output from DAC 206 is directed through multiplexor 208 to the amperometric sensor circuit. The amperage at A/D converters 210–214 is measured and compared to the expected value for corresponding amperometric sensor. If the measured amperage deviates from the expected amount, failure in the corresponding amperometric sensor is likely.

This invention has been described herein in considerable detail in order to comply with the patent statutes and to provide those skilled in the art with the information needed to apply the novel principles and to construct and use such specialized components as are required. However, it is to be understood that the invention can be carried out by specifically different devices, and that various modifications, both as to the equipment details and operating procedures, can be accomplished without departing from the scope of the invention itself.

What is claimed is:

1. A portable analytical instrument having a verification system for verifying the performance of the instrument, said instrument comprising:

(a) a housing;

(b) a multi-channel connector for receiving and electrically connecting to a disposable sensor device attached to said housing;

(c) electronic circuit means for operating said instrument, wherein said electronic circuit means is electrically coupled to said multi-channel connector and a power supply, said electronic circuit means being contained within said housing;

(d) instrument performance verification system contained within said housing including signal generating means for producing internally generated test signals and means for processing performance output signals corresponding to said internally generated test signals, said performance output signals being indicative of the performance of at least one of the group consisting of said multi-channel connector and components of said electronic circuit means, said instrument performance verification system being coupled to said electronic circuit means; and (e) output means in said housing connected to transmit test result signals related to said performance output signals and indicative of results obtained from tests using said instrument performance verification system.

2. The instrument of claim 1, further comprising a plug-in external heater and thermistor electrically connected to said electronic circuit for testing of the calibration of a temperature control system for a disposable sensor device.

3. The instrument of claim 2, wherein said heater and thermistor are contained on a test card adapted to be received by said multi-channel connector.

4. The instrument of claim 1, wherein said verification system includes means for detecting leakage to ground within the electronic circuit.

5. The instrument of claim 1, wherein said verification system includes means for detecting leakage between contacts electrically coupled in the electronic circuit means.

6. The instrument of claim 1, wherein said verification system includes means for determining failure in an amperometric sensor circuit.

7. The instrument of claim 1, wherein said verification system includes means for determining failure in a potentiometric sensor circuit.

8. The instrument of claim 1, wherein said verification system includes means for determining failure in an operational amplifier electrically coupled in the electronic circuit means.

9. The instrument of claim 1, wherein said verification system includes means for determining failure in a conductometric circuit electrically coupled within the electronic circuit means.

10. The instrument of claim 1, wherein said verification system includes means for detecting failure in an AC source for a conductometric sensor circuit electrically coupled to the electronic circuit.

11. The instrument of claim 1, wherein said verification system includes means for detecting failure in a band pass filter for a conductometric sensor circuit electrically coupled to the electronic circuit.

12. A method of testing the integrity of various components which are electrically coupled to diagnostic equipment using one or more test cycles, wherein the diagnostic equipment includes a multi-channel connector for electrical connection to a disposable sensor device, an electronic circuit electrically coupled to said multi-channel connector, a power supply linked to said electronic circuit, and testing means internally connected to said electronic circuit for processing output signals corresponding to internally generated test signals from at least one of the group consisting of said multi-channel connector and components of said electronic circuit, said method comprising the steps of:

(a) activating a test cycle of the diagnostic equipment;

(b) measuring electrical leakage within the electronic circuit;

(c) measuring a pin to pin leakage within the electronic circuit;

(d) measuring a pin to ground leakage within the electronic circuit;

(e) analyzing measurements corresponding to the electrical leakage within the electronic circuit, pin to pin leakage and pin to ground leakage; and (f) indicating results obtained from analyzing measurements corresponding to the electrical leakage within the electronic circuit, pin to pin leakage and pin to ground leakage.

13. The method as recited in claim 12, further comprising the step of determining the A/D reference voltage of the electronic circuit.

14. The method as recited in claim 13, further comprising the step of comparing the A/D reference voltage with a predetermined expected value.

15. The method as recited in claim 12, further comprising the step of determining the integrity of a potentiometric circuit operational amplifier electrically coupled to the electronic circuit.

16. The method as recited in claim 15, further comprising the step of comparing the integrity of the potentiometric operational amplifier with a predetermined expected value.

17. The method as recited in claim 12, further comprising the step of testing a quality of an amperometric sensor circuit.

18. The method as recited in claim 12, further comprising the step of testing a quality of a conductometric sensor circuit.

19. The method as recited in claim 12, further comprising the step of testing a temperature control circuit coupled to said electronic circuit.

20. The method as recited in claim 12, further comprising the step of testing an edge connector contact resistance of said electronic circuit.

21. In a portable analytical instrument having a housing, a multi-channel connector attached to said housing for receiving an electrical connection to a disposable sensor device, and an electronic circuit means for operating said instrument, wherein said electronic circuit means is electrically coupled to said multi-channel connector and a power supply, said electronic circuit means being contained within said housing, a system for verifying the performance of the instrument, said system comprising:

(a) verification system contained within said housing for verifying performance of the instrument, said verification system including signal generating means for producing internally generated test signals and means for processing performance output signals corresponding to said internally generated test signals, said performance output signals being indicative of the level of performance of at least one device selected from the group consisting of elements of said multi-channel connector and selected components of said electronic circuit, said verification system being coupled to said electronic circuit; and output means in said housing connected to transmit signals related to said performance output signals and indicative of results obtained from said verification means.

22. The verification system of claim 21 further comprising means for detecting failure in sensor circuits selected from amperometric and potentiometric sensor circuits.

23. The verification system of claim 22 including spanning means for checking performance of the sensor circuits over a range of electrical values exceeding the normal operating range of each sensor circuit tested.

24. The verification system of claim 21 including means for detecting leakage current selected from leakage between contacts electrically coupled in the electronic circuit means and leakage to ground within the electronic circuit means.

25. The verification system of claim 21 further comprising means for detecting failure in the operation of amplifiers, including operational amplifiers, electrically coupled in the electronic circuit means.

26. In a portable analytical instrument having a housing, a multi-channel connector attached to said housing for receiving and electrically connecting to a disposable sensor cartridge device, and electronic circuit means for operating said diagnostic instrument, wherein said electronic circuit means is electrically coupled to said multi-channel connector and a power supply, said electronic circuit means being contained within said housing, a system for verifying the performance of the instrument, said system comprising:

(a) passive externally connected test card means for testing the calibration of a temperature control system for controlling the temperature of said disposable sensor cartridge device, said test card means being one that removably electrically connects to said electronic circuit means; and (b) output means indicative of results obtained from using said test card means.

27. The performance verification system of claim 26 wherein said passive externally connected test card means further comprises an integral heater and thermistor.

28. The performance verification system of claim 27 wherein said passive externally connected test card means includes means for verifying integrity of said multi-channel connector.

* * * * *